(12) United States Patent
Sakai et al.

(10) Patent No.: US 8,062,882 B2
(45) Date of Patent: Nov. 22, 2011

(54) APPARATUS FOR CAPTURING CELL

(75) Inventors: Satoru Sakai, Kawasaki (JP); Moritoshi Ando, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 595 days.

(21) Appl. No.: 11/287,384

(22) Filed: Nov. 28, 2005

(65) Prior Publication Data

US 2006/0223163 A1 Oct. 5, 2006

(30) Foreign Application Priority Data

Mar. 31, 2005 (JP) ................. 2005-102094

(51) Int. Cl.
*C12M 3/00* (2006.01)
*C12M 1/00* (2006.01)
(52) U.S. Cl. ............... 435/285.1; 435/285.2; 435/287.1; 435/288.5; 435/288.7; 435/297.2; 359/398; 204/403.01
(58) Field of Classification Search .............. 435/285.1, 435/288.5, 288.4, 285.2, 287.1, 288.7, 297.2, 435/297.5; 359/398; 204/403.01
See application file for complete search history.

(56) References Cited

U.S. PATENT DOCUMENTS

| | | | |
|---|---|---|---|
| 4,729,949 A * | 3/1988 | Weinreb et al. ........... | 435/30 |
| 4,894,343 A * | 1/1990 | Tanaka et al. ........... | 435/285.2 |
| 5,262,128 A * | 11/1993 | Leighton et al. ........... | 422/100 |
| 6,383,813 B1 | 5/2002 | Baxter et al. | |
| 2002/0094567 A1 | 7/2002 | Huberman et al. | |
| 2004/0235143 A1 | 11/2004 | Sasaki et al. | |

FOREIGN PATENT DOCUMENTS

| | | |
|---|---|---|
| DE | 699 07 249 | 1/2004 |
| EP | 0 311 059 | 4/1989 |
| EP | 1 479 759 | 11/2004 |
| EP | 1 582 593 | 10/2005 |
| JP | 2004-163 | 1/2004 |
| JP | 2004-166653 A | 6/2004 |
| JP | 2004-180555 | 7/2004 |
| JP | 2004180555 A * | 7/2004 |
| JP | 2004-344036 A | 12/2004 |
| WO | WO 0020554 A1 * | 4/2000 |
| WO | 01/19978 | 3/2001 |

OTHER PUBLICATIONS

Japanese Office Action (Decision of patent grant), mailed on Aug. 24, 2010 for Japanese Patent Application No. 2005-102094. English-language translation is provided.

* cited by examiner

*Primary Examiner* — William H Beisner
*Assistant Examiner* — Danielle Henkel
(74) *Attorney, Agent, or Firm* — Fujitsu Patent Center

(57) ABSTRACT

A bottom wall of a Petri dish used for capturing a cell is provided with a first through hole and a second through hole. A grove that connects the first through hole and the second through hole is formed on an outer surface of bottom wall. The first through hole, the second through hole, and the grove is covered with a transparent plate member. A plate used for capturing the cell is arranged in the Petri dish above the first through hole. An aspiration tube is connected to the second through hole from inside the Petri dish.

10 Claims, 12 Drawing Sheets

APPARATUS FOR CAPTURING CELL

BACKGROUND OF THE INVENTION

1. Field of the Invention

The present invention relates to an apparatus for capturing a cell for injecting a substance such as a gene or drug into the cell. More specifically, the invention relates to an apparatus that allows observation of the cell while the substance is being injected in the cell.

2. Description of the Related Art

The injection (introduction) of genes or drugs into cells using a needle to alter their properties has recently been carried out in the life science fields, and particularly in the fields of regenerative medicine and genome drug development. When injecting a gene or drug into a cell, it is necessary to immobilize the cell to prevent it from moving. A cell immobilizing plate (hereinafter, "cell capturing plate") has been conventionally used to immobilize a cell. The cell capturing plate has a plurality of microscopic capturing holes. The diameter of these holes is smaller than that of the cells. The diameter of the cells can vary from 10 micrometers to 100 micrometers depending on the type of the cells. Cells are caught, and thereby immobilized, in these holes when the cells, or a liquid containing the cells, is aspirated from the other side of the cell immobilizing plate with an aspiration pump.

A microinjection method has been developed as a method for injecting a gene or drug directly into a cell through a needle. In the microinjection method, an ultrafine needle having a diameter of 1 micrometer or less (tip outer diameter: 1 micrometer, inner diameter: about 0.5 micrometers) and filled with a drug is inserted into a cell and the drug is injected into the immobilized cell. This process is performed while observing the cell and the needle under a microscope.

Petri dishes used in the conventional cell capturing apparatus require a capturing plate that captures cells, a well for holding a cell turbid solution, and on the bottom, a connection for an aspiration tube from an aspiration pump used to aspirate cells into microscopic capturing holes in the capturing plate. Consequently, a structure is mainly employed for conventional Petri dishes for cells in which microscopic holes are formed at predetermined positions in a Petri dish, a cell capturing plate is adhered to form a well, and the Petri dish is placed on a unit that was machined to serve as an aspiration connector from an aspiration pump.

FIG. 17 is a schematic block diagram of a Petri dish used in a conventional cell capturing apparatus. A cell turbid solution is contained inside a Petri dish 100a, a through hole 112 is formed approximately in the center of the Petri dish 100a, and a capturing plate 30 is fixed on the through hole 112 by adhesion and the like.

A plurality of micropores 330 are formed in the capturing plate 30. Cells are captured in these micropores 330 by aspirating the cell turbid solution from below with an aspiration pump 200 through the through hole 112. The captured cells can be observed with a microscope (not shown) from above the Petri dish 100a.

Conventional techniques relating to capturing of cells have been disclosed, for example, in Japanese Patent Application Laid-open No. 2004-180555 and Japanese Patent Application Laid-open No. 2004-163.

In the conventional Petri dish 100a, there has been a problem of the occurrence of leakage from a gap between the Petri dish 100a and the capturing plate 30, thereby preventing the necessary cells from being aspirated (captured) reliably.

It is a common practice to observe the cells with a transmitted light. Since the well and aspiration connection are molded into a single unit as a result of machining in a conventional Petri dish as previously described, however, the machined surface on the bottom of the capturing plate cannot be optically polished, thereby resulting in the problem of being unable to observe the cells from below the capturing plate with transmitted light.

Furthermore, there are no particular considerations given to the handling of injected cells, which are cells in which a substance has been injected, and empty cells, which are cells in which the substance has not been injected because they are not suitable for injection of the substance. Since a technique capable of distinguishing between these injected cells and empty cells has not been examined, a method of distinguishing these injected cells and empty cells is desired.

SUMMARY OF THE INVENTION

It is an object of the present invention to at least solve the problems in the conventional technology.

According to an aspect of the present invention, a cell capturing apparatus, which is suitably used to capture a cell and inject a substance into captured cell while observing the cell under a microscope, includes a cell capturing container having a bottom wall and a side wall, the bottom wall including a first through hole; a second through hole; and a groove that connects ends of the first through hole and the second through hole that open on outer surface of the bottom wall; a transparent plate member that covers a portion of the outer surface of the bottom wall including at least the first through hole, the second through hole, and the groove; a capturing plate disposed inner surface of the bottom wall and above the first through hole; and an aspiration tube with one end connected to an upper portion of the second through hole and other end connected to an aspirating unit.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention are explained below in detail with reference to the accompanying drawings. The following explains a summary and characteristics of the structure of the Petri dish according to each embodiment. It is followed by a detailed explanation of the functions resulting from the constitution of the Petri dish, and the constitutions and functions relating to an empty-cell collecting member mounted to the Petri dish and a multifunctional flow path plate.

A Petri dish 100 according to a first embodiment is explained below. This Petri dish 100 is characterized in preventing leakage, which has been a problem in the conventional techniques, and facilitating observation of captured cells.

An aspiration system is provided above the Petri dish 100, and together with aspirating cells from above, a flow path formed on the Petri dish 100 is made to facilitate observation of captured cells by sealing with a transparent plate member 400 from below the Petri dish 100.

Figure 1:
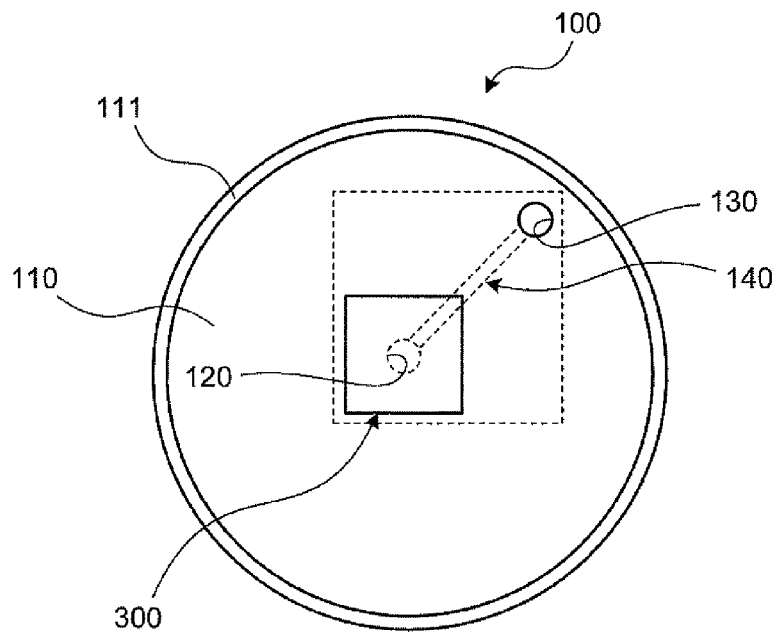
FIG. 1 is a top view of a Petri dish according to a first embodiment of the present invention.

The Petri dish 100 is explained in detail with reference to FIGS. 1 and 2. FIG. 1 is a top view and FIG. 2 is a longitudinal cross-section of the Petri dish 100.

Figure 2:
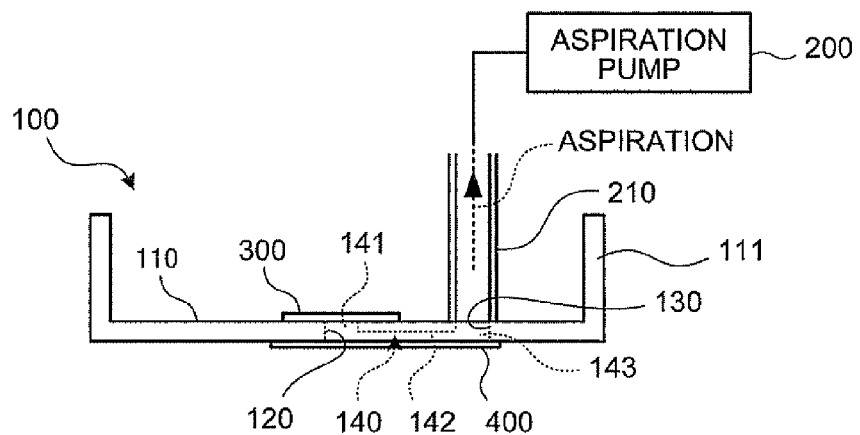
FIG. 2 is a longitudinal cross-section of the Petri dish shown in FIG. 1.

Namely, as shown in FIGS. 1 and 2, the Petri dish 100 is formed from a circular base (a bottom wall 110) and a peripheral wall 111, and two through holes 120 and 130, which are mutually separated and open upward, and an intake flow path 140 for aspirating cells, are formed on the bottom wall 110 of the Petri dish 100. The intake flow path 140 is composed by connecting a first flow path 141 continuous with the through hole 120, a second flow path 142, and a third flow path 143 continuous with the through hole 130.

The lower side of the intake flow path 140 is sealed by the transparent plate member 400. Accordingly, a closed flow path is formed within the intake flow path 140 through which intake air passes from the aspiration pump 200. Furthermore, although the intake direction of the intake flow path 140 is provided on the upper side in this example, the intake flow path 140 can be also made to, for example, intake from the horizontal direction of the Petri dish 100.

A capturing plate 300 is fixed by adhesion and the like to the portion corresponding to the formed position of the through hole 120 approximately in the center of the bottom wall 110. More specifically, the attached position of the capturing plate 300 is selected so that the through hole 120 is positioned approximately in the center of the capturing plate 300.

This is because cells on the capturing plate 300 are reliably aspirated through a plurality of micropores 330 formed on the capturing plate 300 as will be described later. On the other hand, an aspiration tube 210 for intake of air from the intake flow path 140 is attached by adhesion and the like to upwardly opening the through hole 130 through a coupling (not shown).

The transparent plate member 400 is sealed by affixation to the position below the capturing plate 300 where the through hole 120 and the second flow path 141 are formed. Consequently, the transparent plate member 400 has a function of serving as a distribution route by covering the intake flow path 140 formed on the Petri dish 100 from below, and a function for observing cells with transmitted light.

Figure 3:
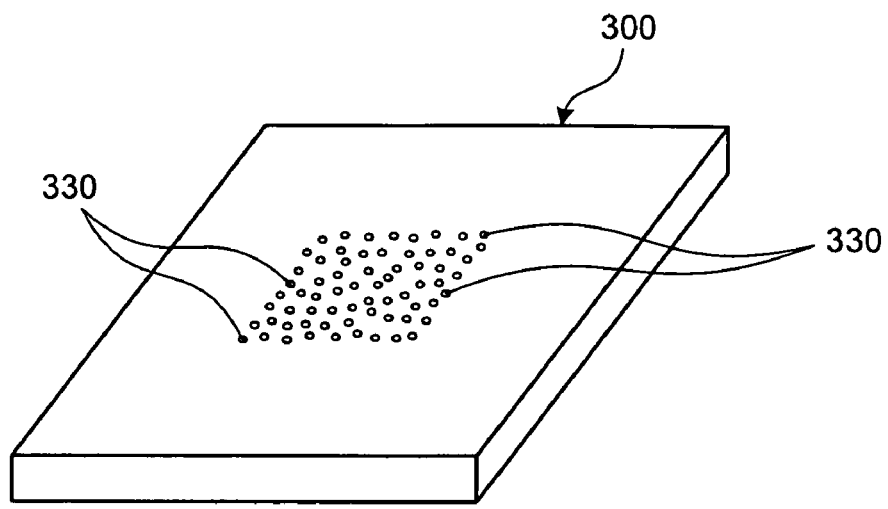
FIG. 3 is a perspective view (front side view) of a capturing plate according to the first embodiment.
Figure 4:
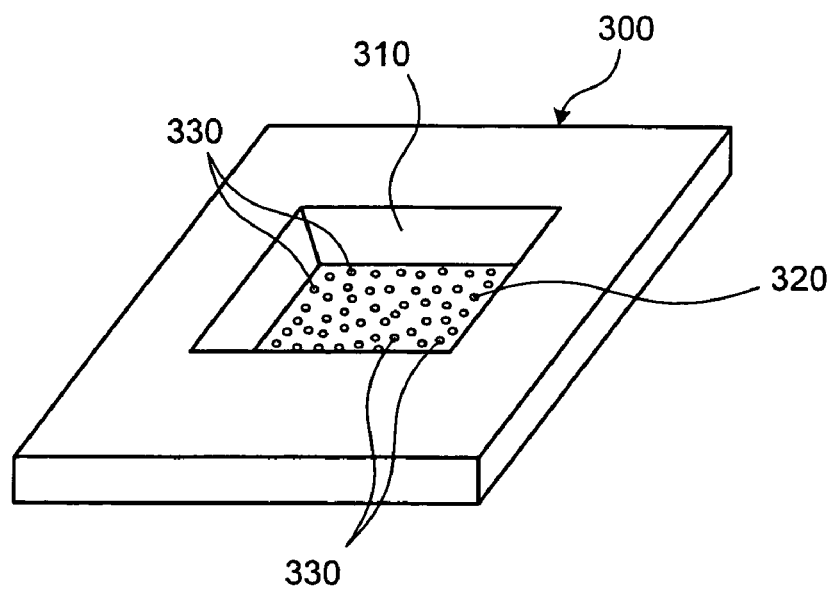
FIG. 4 is a perspective view (back side view) of the capturing plate shown in FIG. 3.

The characteristics and structure of the capturing plate 300 shown in FIGS. 1 and 2 are explained in detail with reference to FIGS. 3 and 4. FIG. 3 is a perspective view (front side view) of the capturing plate 300 attached to the Petri dish 100. FIG. 4 is a perspective view (back side view) of the capturing plate 300 in an inverted state as viewed from the side of the transparent plate member 400.

Namely, as shown in FIGS. 3 and 4, the capturing plate 300 is composed in the shape of a square, an upwardly opening rectangular concave portion 310 is formed approximately in its center, and a plurality of the micropores 330 are randomly formed on the lower surface 320 of the concave portion 310. The micropores 330 are formed for the purpose of capturing cells through the first flow path 141 of the intake flow path 140 with intake air that has been aspirated through the aspiration pump 200 and the aspiration tube 210. This aspiration allows cells to be captured in the capturing plate 300.

The diameter of the micropores 330 is determined according to the size of the cells to be captured. For example, in the case of attempting to capture cells having a diameter of about 10 to 20 micrometers, the diameter of the micropores 330 is set to that which is smaller than the diameter of these cells.

Since the micropores 330 formed on the capturing plate 300 have a large aspect ratio, the portion where the micropores 330 are formed must be thin. However, since reducing the thickness of the entire capturing plate 300 results in decreased strength, in this example, together with using a silicon material for the composite material of the capturing plate 300, only the portion where the micropores 330 are formed (the lower surface 320) is made to be thin. The use of such a structure makes it possible to maintain the strength of the capturing plate 300 itself.

As has been explained above, according to the first embodiment, the Petri dish 100 employs a constitution that a pair of the through holes 120 and 130 are formed at two positions on the bottom wall 110, the intake flow path 140 is formed that connects the lower openings of these through holes 120 and 130, the transparent plate member 400 is provided that seals the intake flow path 140 from below the bottom wall 110, the capturing plate 300 is disposed at the position of the upper opening formed by the through hole 120, and the aspiration tube 210 continuous with the aspiration pump 200 is connected to the upper opening of the through hole 130. Thus, cells can be reliably aspirated without the occurrence of problems such as leakage. Cells can be also easily observed with transmitted light through the transparent plate member 400.

A second embodiment of a cell capturing apparatus of the present invention is explained in detail. Namely, as shown in FIGS. 5A, 5B, 6, and 7, the second embodiment is characterized by having an empty-cell collection plate 500 for collecting empty cells mounted on the Petri dish 100 in addition to an aspiration route (the intake flow path 140) formed at the bottom of the Petri dish 100.

Injected cells and empty cells are both present on the surface of the capturing plate 300. Thus, in the second embodiment, by mounting the empty-cell collection plate 500 within the Petri dish 100, these empty cells can be collected and removed efficiently.

Figure 5A:
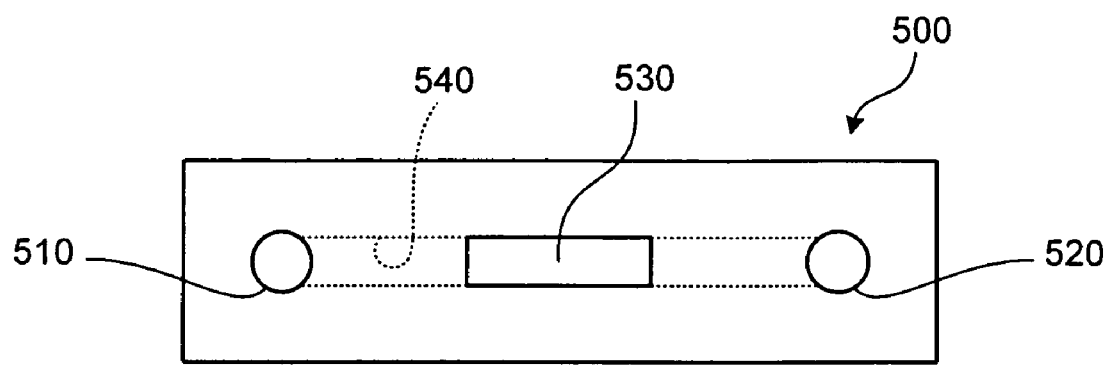
FIG. 5A is a top view of an empty-cell collection plate according to a second embodiment of the present invention.
Figure 5B:
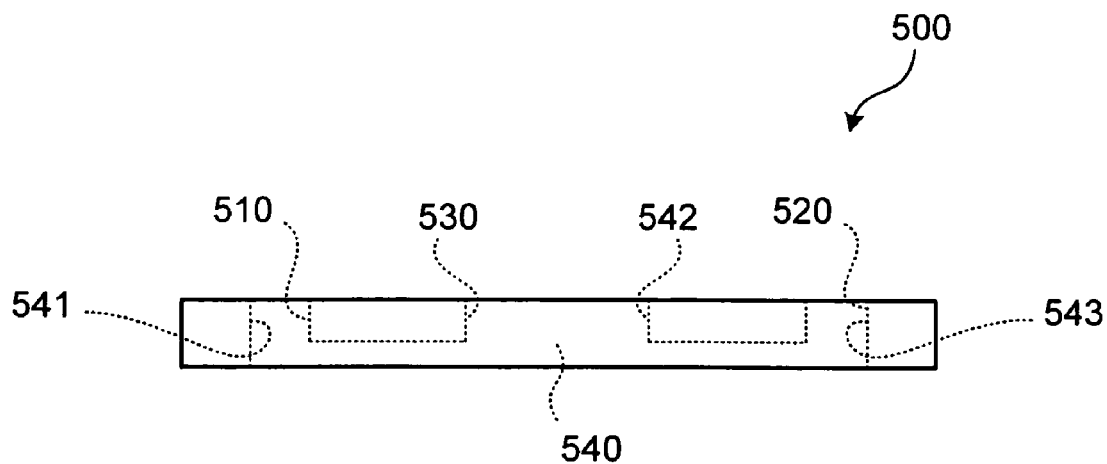
FIG. 5B is a longitudinal cross-section of the empty-cell collection plate shown in FIG. 5A.
Figure 6:
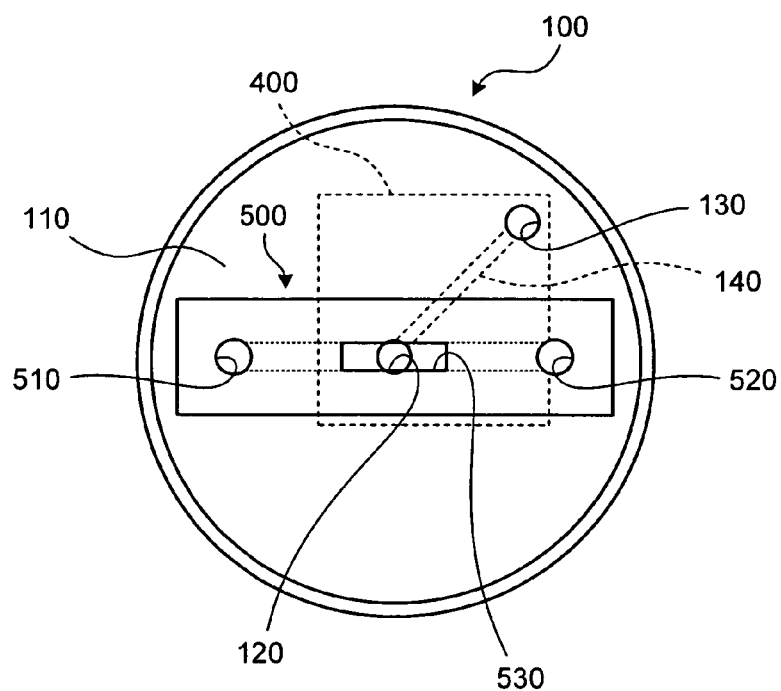
FIG. 6 is a top view of a Petri dish on which the empty-cell collection plate shown in FIG. 5A is mounted.
Figure 7:
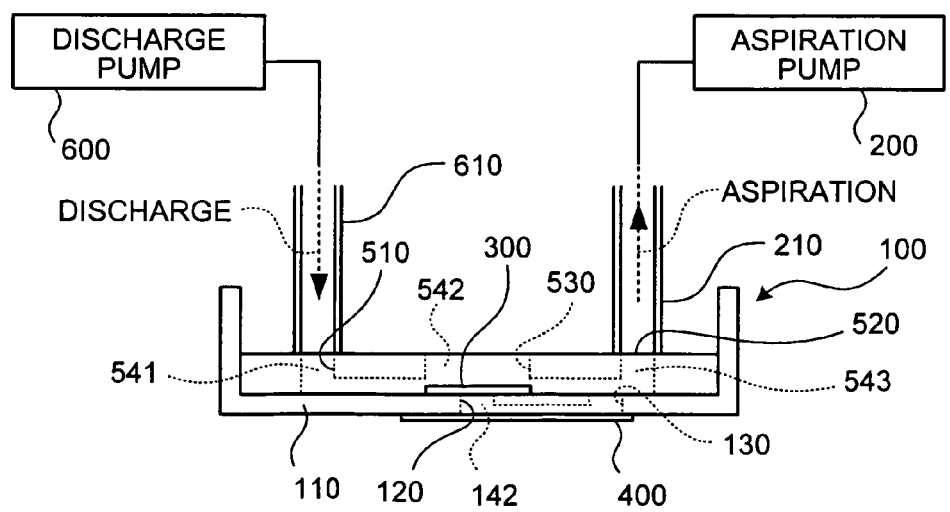
FIG. 7 is a longitudinal cross-section of a Petri dish on which the empty-cell collection plate shown in FIG. 5A is mounted along with some other relevant parts.

The characteristics and functions of the empty-cell collection plate 500 are explained in detail with reference to FIGS. 5A, 5B, 6, and 7. FIG. 5A is a top view and FIG. 5B is a longitudinal cross-section of the constitution of the empty-cell collection plate 500. FIG. 6 is a top view of the Petri dish 100 on which the empty-cell collection plate 500 is mounted, and FIG. 7 is their respective longitudinal cross-sections. As shown in FIGS. 6 and 7, the empty-cell collection plate 500 is attached by adhesive and the like to the bottom wall 110 of the Petri dish 100.

As shown in FIGS. 5A, 5B, 6, and 7, the empty-cell collection plate 500 is composed in the shape of a square having nearly the same dimensions as the inner diameter of the Petri dish 100, and a pair of the through holes 510 and 520 at both ends and an injection opening 530 approximately in the center are formed together with a collection flow path 540.

Two through holes 510 and 520, which are mutually separated and open upward, and the collection flow path 540, through which collection liquid flows, are formed on the empty-cell collection plate 500, and the collection flow path 540 is composed by connecting a first flow path 541 continuous with the through hole 510, a second flow path 542, and a third flow path 543 continuous with the through hole 520.

Since the bottom of the collection flow path 540 is sealed by the upper surface of the bottom wall 110 of the Petri dish 100, a flow path is formed that distributes collection liquid within the empty-cell collection plate 500.

The through hole 510 functions as a liquid (cell turbid solution, culture liquid, or physiological saline) discharge hole, and a discharge tube 610 of a discharge pump 600 for discharging cleaning water is connected to the through hole 510. The aspiration tube 210 of the aspiration pump 200 is connected to the through hole 520.

Figure 8A:
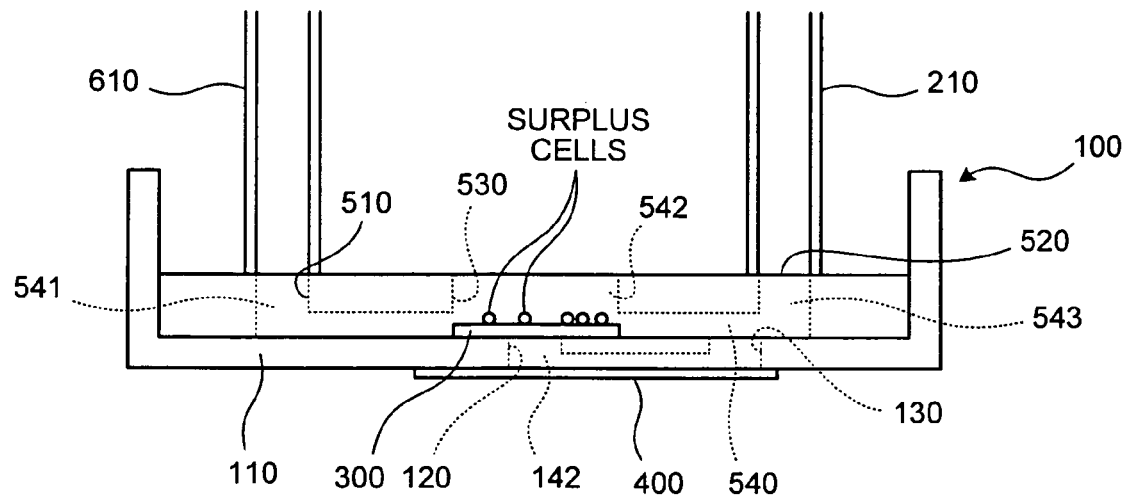
FIG. 8A is an explanatory diagram of the state prior to collection of empty cells.
Figure 8B:
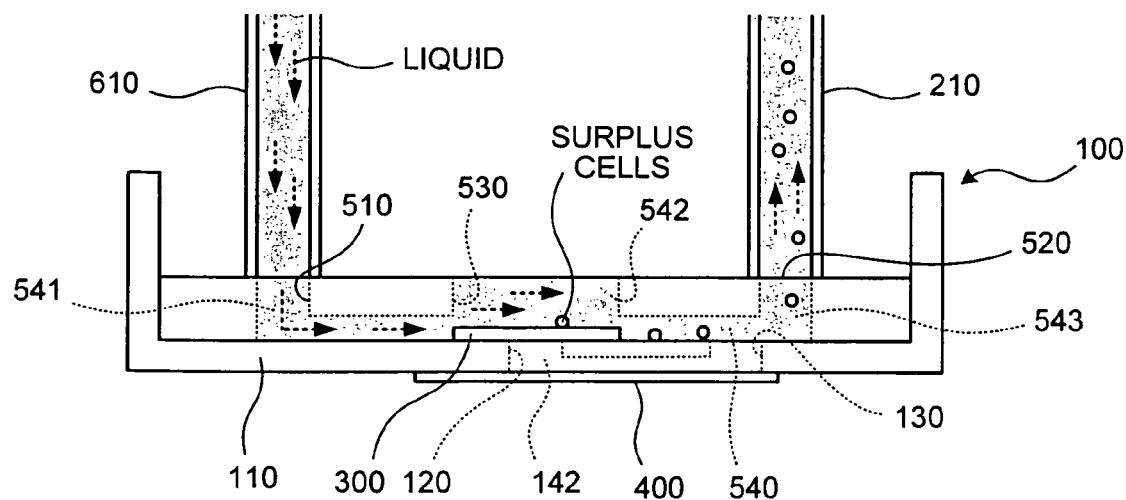
FIG. 8B is an explanatory diagram of the state during collection of the empty cells.

Collection of the empty cells by the empty-cell collection plate 500 is explained with reference to FIGS. 8A and 8B. FIG. 8A is a diagram of the state prior to collecting the empty cells, and at this time, as shown in FIG. 8B, as a result of physiological saline supplied from the discharge pump 600 flowing through the discharge tube 610 and passing through the first flow path 541 continuous with the through hole 510, the second flow path 542, and the third flow path 543 continuous with the through hole 520, the empty cells near the capturing plate 300 flow and are collected at the outside through the aspiration tube 210.

As a result, unnecessary empty cells can be collected efficiently while allowing the necessary injected cells to remain in the cell capturing plate 300. The liquid discharged as collection liquid from the discharge pump 600 (cell turbid solution, culture liquid, or physiological saline) can use the same liquid as the liquid used for injection.

Although the function of the empty-cell collection plate 500 of the second embodiment is mainly to collect the empty cells, it can be also used as an injection liquid supply apparatus for supplying a liquid (cell turbid solution, culture liquid, or physiological saline) to the Petri dish 100 when simply carrying out cell injection.

As has been explained above, since the second embodiment is composed by mounting the empty-cell collection plate 500 for collecting unnecessary empty cells within the Petri dish 100, in addition to being able to easily distinguish between the injected cells and the empty cells within the Petri dish 100, which has not been achieved by the conventional techniques, the necessary injected cells remain in the capturing plate 300, while unnecessary empty cells can be efficiently collected.

Figure 9A:
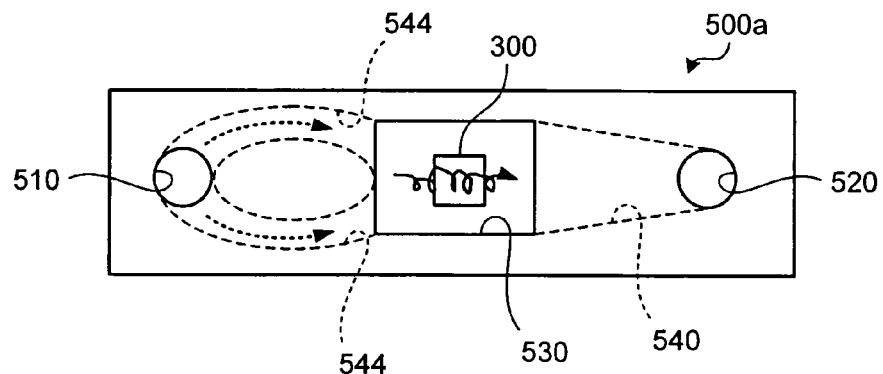
FIG. 9A is a top view of an empty-cell collection plate according to a first example.

Variations of the empty-cell collection plate of the second embodiment are explained in detail with reference to FIGS. 9A to 9C. FIG. 9A is a first example of the structure of an empty-cell collection plate 500a. As shown in FIG. 9A, this example is characterized by employing a constitution that the flow path from the through hole 510 to the capturing plate 300 is in the form of a branched flow paths 544, and by supplying liquid from these flow paths 544 (multiple discharge flow paths), an eddy flow path is formed near the position where the capturing plate 300 is disposed.

Since liquid flows in from these multiple flow paths 544, eddy flow is generated near the capturing plate 300, thereby enabling empty cells to be removed. Accordingly, only the necessary cells can be captured.

Figure 9B:
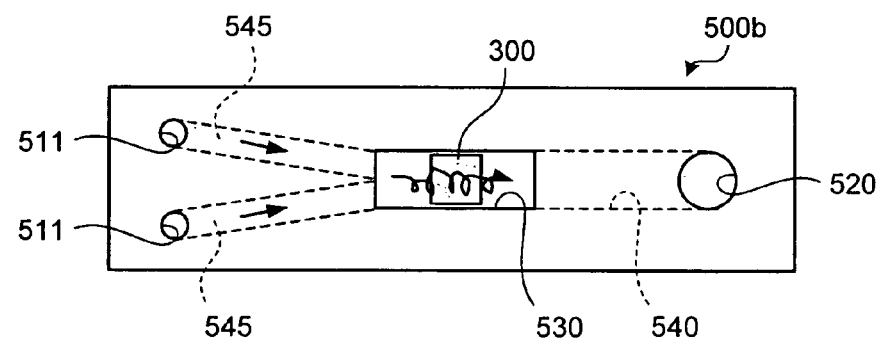
FIG. 9B is a top view of an empty-cell collection plate according to a second example.

FIG. 9B is a second example of the structure of the empty-cell collection plate 500b. As shown in FIG. 9B, this example employs a constitution that flow paths 545, 545 respectively connected to two through holes 511, 511 form a branched flow path. In this second example, since the force of the liquid that flows from the flow paths 545, 545 in two directions increases, empty cells can be removed more effectively.

In this case, when discharging liquid from each of the two through holes 511, 511, the characteristics of each liquid can be changed. For example, eddy flow can be generated more easily by changing conditions such as concentration and temperature.

Figure 9C:
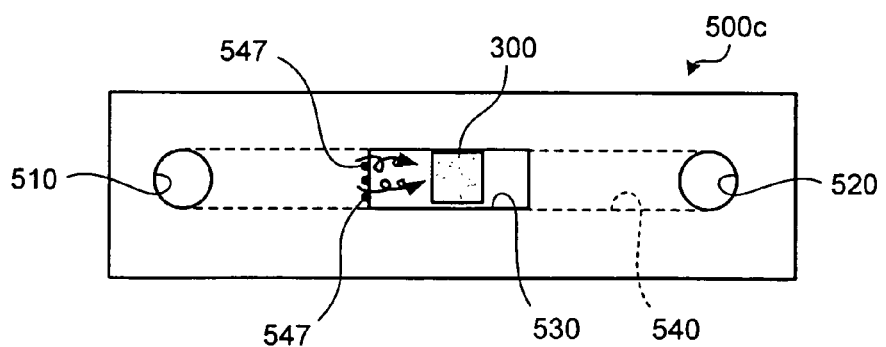
FIG. 9C is a top view of an empty-cell collection plate according to a third example.

FIG. 9C is a third example of the structure of the empty-cell collection plate 500c. As shown in FIG. 9C, this example is characterized by providing a plurality of convex portions 547 at the position of the initial flow path that leads to the capturing plate 300. Namely, since these convex portions 547 serve as obstructions in the flow path, when water that flows in from the first flow path 541 has reached these convex portions 547, the flow path is dispersed, resulting in the formation of eddy flow near the capturing plate 300 and enabling empty cells to be removed more effectively.

Figure 10:
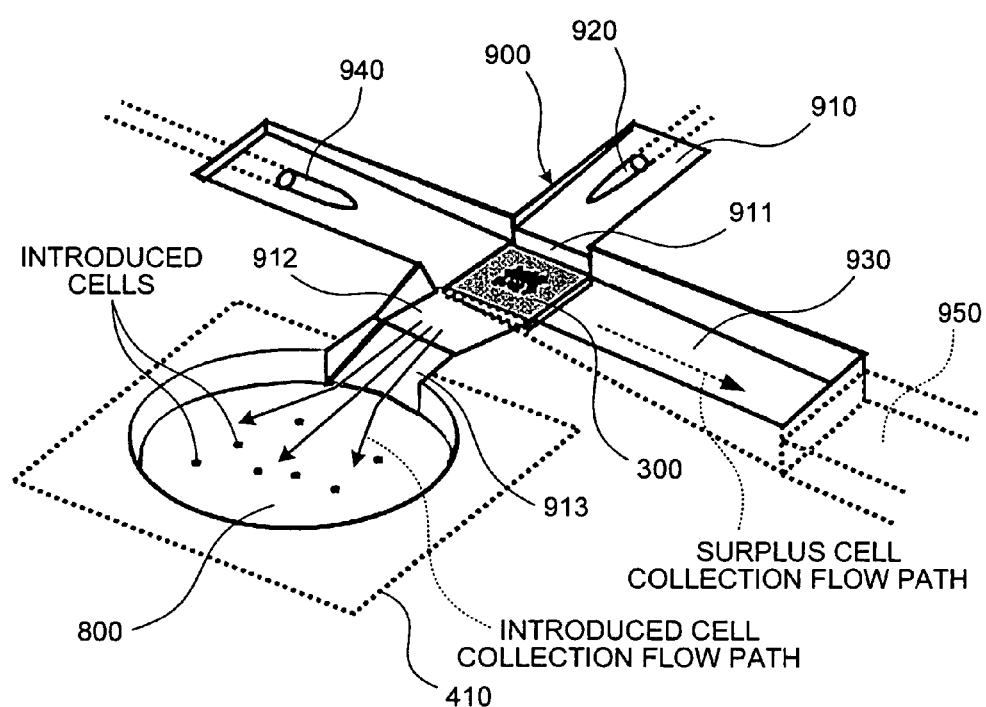
FIG. 10 is a perspective view of a multifunctional flow path plate according to a third embodiment of the present invention with other relevant parts.

A third embodiment of the cell capturing apparatus according to the present invention is explained in detail with reference to FIG. 10. FIG. 10 is a perspective view of the constitution of a multifunctional flow path plate 900. As shown in FIG. 10, the third embodiment is characterized by employing a constitution that the multifunctional flow path plate 900 is provided in the cell capturing apparatus, and the multifunctional flow path plate 900 includes (1) a function that supplies cells, culture liquid and the like, (2) a function that collects empty cells, (3) a function for allowing cells that have been injected (injected cells) to flow, and (4) a function that collects the injected cells.

Namely, as shown in FIG. 10, the multifunctional flow path plate 900 has an injected-cell collecting flow-path 910 for allowing injected cells to flow and collecting those injected cells, and an empty-cell collecting flow-path 930 for allowing empty cells to flow and collecting those empty cells, that cross nearly perpendicularly. The capturing plate 300 is provided at the position (center) where the injected-cell collecting flow-path 910 and the empty-cell collecting flow-path 930 respectively cross.

A discharge port 920 from which liquid is discharged is formed in the upstream end (upper side of FIG. 10) of the injected-cell collecting flow-path 910, and an observation well 800 formed into a circular shape for observing cells is provided at the downstream end (lower side of FIG. 10). Introduced cells that have flowed from the capturing plate 300 are made to flow into the observation well 800 by liquid discharged from the discharge port 920, and a transparent plate member 410 that uses a glass material and the like is affixed to the bottom of the observation well 800. As a result, injected cells that have flowed into the observation well 800 can be easily observed with transmitted light or fluorescent light through the transparent plate member 410.

A first inclination 912, which inclines upward from the position of the upper surface of the capturing plate 300, and a second inclination 913, which inclines downward from the apex of the first inclination 912 towards the observation well 800, are provided between the capturing plate 300 and the observation well 800. In other words, by providing the first and the second inclinations 912 and 913 at an intermediate position in the flow path from the capturing plate 300 to the observation well 800, injected cells that have flowed into the observation well 800 are effectively prevented from flowing back outside the observation well 800.

Furthermore, a step 911, the position of which lowers as it approaches the capturing plate 300, is provided in the multifunctional flow path plate 900 at the position where the flow path for collecting injected cells and the flow path for collecting empty cells intersect to prevent mixing of empty cells and injected cells.

A discharge port 940 from which liquid is discharged is formed in the upstream end (left side of FIG. 10) of the empty-cell collecting flow-path 930, and an empty cell collection port 950 for collecting empty cells is provided in the downstream end (right side of FIG. 10). Surplus cells present near the capturing plate 300 are made to flow into the empty cell collection port 950 by liquid discharged from the discharge port 940.

During collection of injected cells and empty cells by the multifunctional flow path plate 900, the times at which liquid is allowed to flow differ between the case of collecting injected cells and the case of collecting empty cells. In the case of supplying cells or culture liquid to the Petri dish 100, either the liquid discharge port 920 or the liquid discharge port 940 is used.

Figure 11:
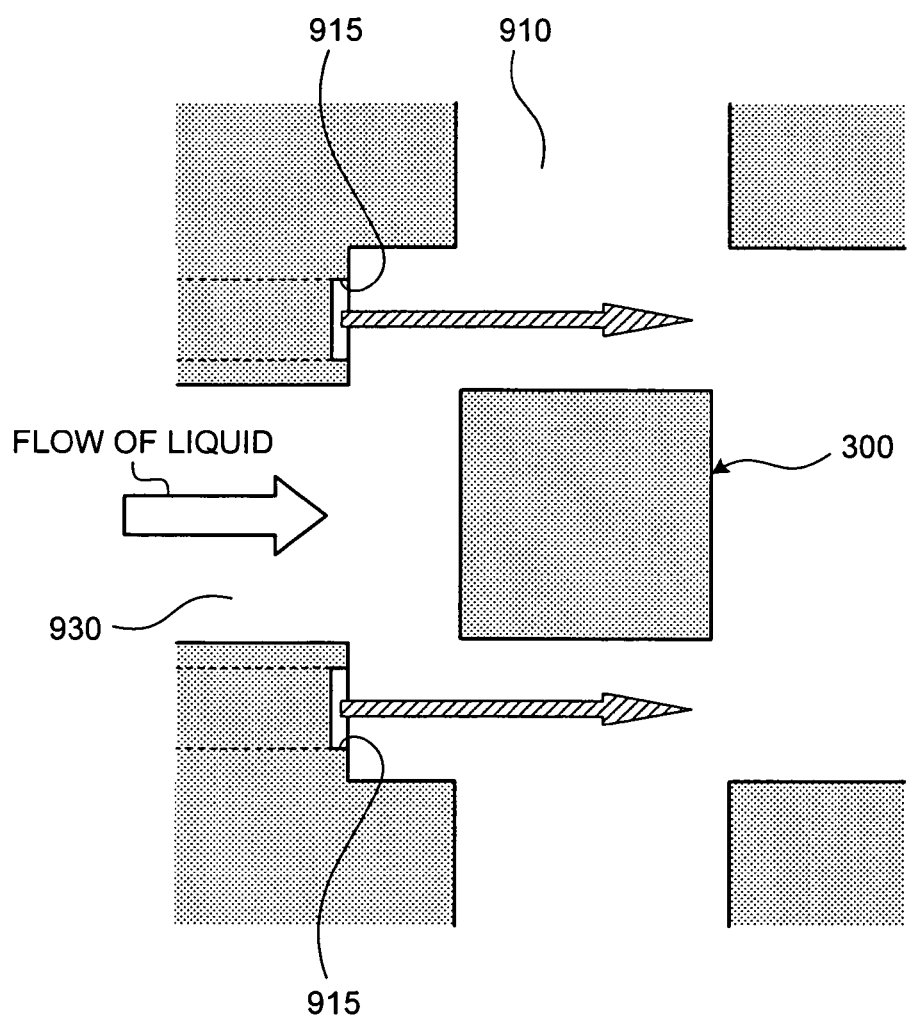
FIG. 11 is a top view of relevant parts of the multifunctional flow path plate shown in FIG. 10.

FIG. 11 is a top view of a shield flow path for preventing mixing of the empty cells and the injected cells. Namely, as shown in FIG. 11, the third embodiment is characterized by respectively forming discharge ports 915 from which cleaning liquid flows at both ends of the discharge port 920 for removal of the empty cells. More specifically, liquid is first made to flow from a pair of the liquid discharge ports 915 provided on the left and right sides before carrying out an empty cell removal step.

As a result, since a so-called shield flow path (a curtain of path) is formed, the flow of the empty cells into the discharge port 920 for injected cells and the discharge port 940 for collection in the observation well 800 can be reliably prevented. At this time, since the flow rate when injected cells are allowed to flow is faster than the flow rate when the empty cells are allowed to flow, shielding effects are further improved, thereby making it possible to prevent mixing of the empty cells and the injected cells.

Figure 12:
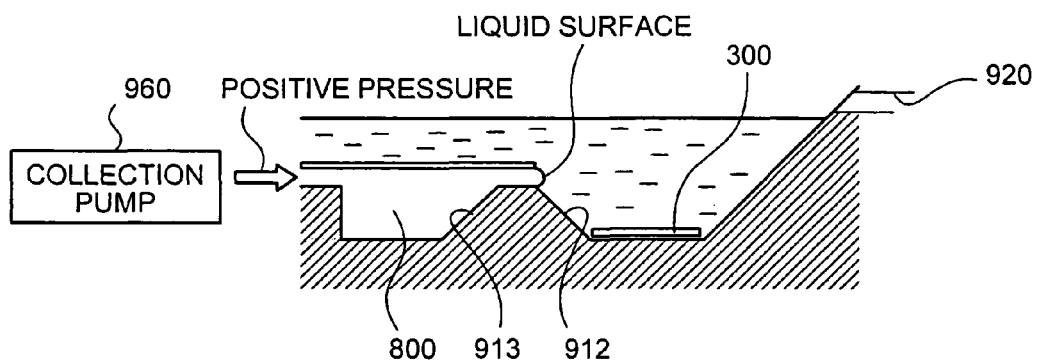
FIG. 12 is a longitudinal cross-section of the state prior to collection of injected cells in the multifunctional flow path plate shown in FIG. 10.
Figure 13:
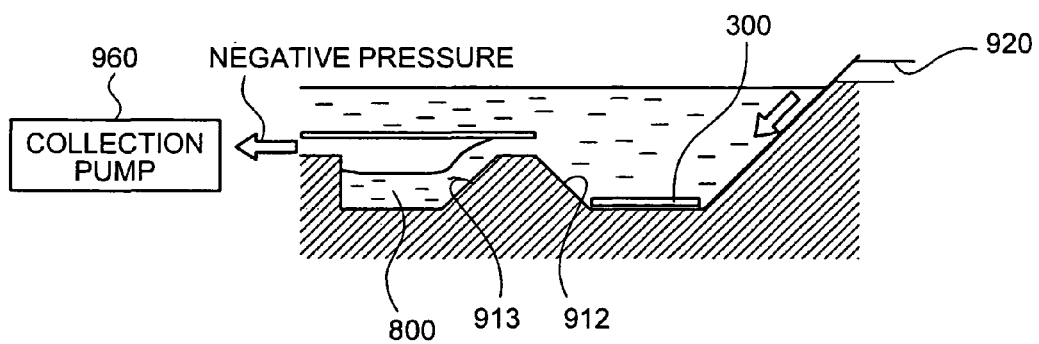
FIG. 13 is a longitudinal cross-section of the state during collection of the injected cells in the multifunctional flow path plate shown in FIG. 10.

An example of a collection method for injected cells using the multifunctional flow path plate 900 is explained with reference to FIGS. 12 and 13. FIG. 12 is a cross-section of relevant parts shown in FIG. 11, and depicts the state prior to collecting injected cells. FIG. 13 is also a cross-section of the relevant parts shown in FIG. 11, and depicts the state during collection of injected cells. Namely, in this example, a collection pump 960 for collecting injected cells is provided at one end of the well 800, and by varying the aspiration pressure generated by the collection pump 960 (between positive pressure and negative pressure), the injected cells and the empty cells are prevented from mixing. More specifically, the collection pump 960 is controlled so as to generate positive aspiration pressure prior to collecting injected cells as shown in FIG. 12.

In this case, as shown in FIG. 12, liquid does not penetrate into the observation position of the well 800. Accordingly, liquid can be prevented from flowing into the well 800. On the other hand, the collection pump 960 is controlled by switching its aspiration pressure from positive pressure to negative pressure when collecting injected cells. Accordingly, as shown in FIG. 13, injected cells flow into the well 800 together with a cell turbid solution discharged from the liquid discharge port 920 (FIG. 11), enabling these injected cells to be observed.

A fourth embodiment of the present invention is explained in detail with reference to FIG. 14. The fourth embodiment is characterized by employing a method of fixing the capturing plate 300 to the Petri dish 100 (joined orientation of the capturing plate 300). Namely, when observing cells by transmitted light with a microscope provided in the cell capturing apparatus, although a cell turbid solution (culture liquid) present in the concave portion 310 of capturing plate 300, air and the transparent plate member 400 are present between the capturing plate 300 and the objective lens of the microscope, if air bubbles are present between the transparent plate member 400 and the capturing plate 300, cells cannot be observed satisfactorily. Thus, cells are observed in the state in which culture liquid is filled between the transparent plate member 400 and the capturing plate 300.

Since the optical resolution during microscopic observation is affected by the thickness of the culture liquid, when culture liquid is filled into the concave portion 310 of the capturing plate 300, optical resolution decreases. Decreases in optical resolution can therefore be prevented by reducing the thickness (amount filled) of the culture liquid. In focusing on this point, the fourth embodiment employs a constitution that the separation distance between the transparent plate member 400 adhered to the bottom of the Petri dish 100 and the capturing plate 300 is shortened.

Figure 14:
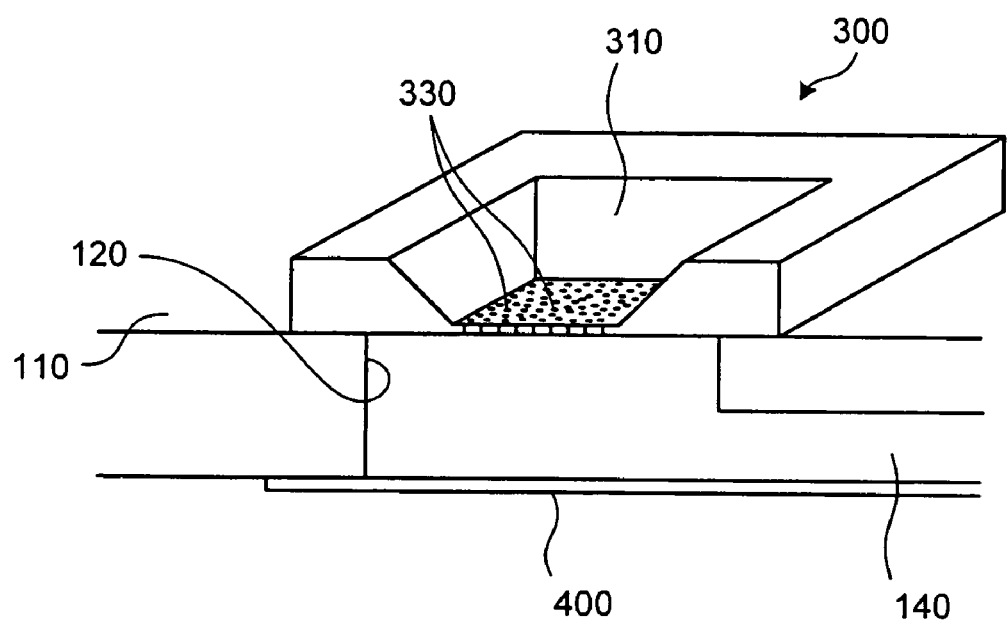
FIG. 14 is a perspective view of a capturing plate according to a fourth embodiment of the present invention.

More specifically, as shown in FIG. 14, differing from the orientation in which the capturing plate 300 is joined as shown in the first embodiment, the lower surface 320 of the capturing plate 300 contacts the bottom wall 110 of the Petri dish 100. According to the constitution of the fourth embodiment, the distance between the transparent plate member 400 and the capturing plate 300 can be shortened, and the thickness to which culture liquid is filled can therefore be reduced. Accordingly, decreases in optical resolution of the culture liquid during observation can be prevented.

A constitution can be also employed in which the lower surface of the capturing plate 300 is made to be slightly embedded in the bottom wall 110 of the Petri dish 100, thereby making it possible to shorten the distance between the transparent plate member 400 and the capturing plate 300.

As has been explained above, since the fourth embodiment is composed by allowing the lower surface of the capturing plate 300 to contact the bottom wall 110 of the Petri dish 100, the separation distance between the transparent plate member 400 and the capturing plate 300 can be shortened, and the thickness to which culture liquid is filled can therefore be reduced, thereby making it possible to prevent decreases in optical resolution during microscopic observation.

Figure 15A:
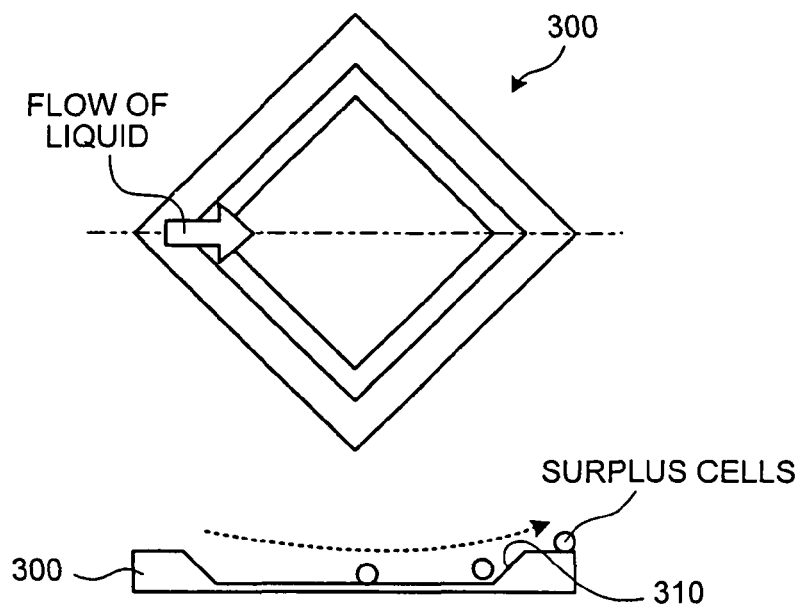
FIG. 15A is an explanatory diagram to explain an example of an orientation of a capturing plate according to a fifth embodiment of the present invention.

A fifth embodiment of the present invention is explained in detail with reference to FIGS. 15A and 15B. FIG. 15A is a schematic view of the direction in which the capturing plate 300 is joined to the Petri dish 100 according to the fifth embodiment, and FIG. 15B is a schematic view of the direction in which the capturing plate 300 is joined to the conventional Petri dish 100.

Figure 15B:
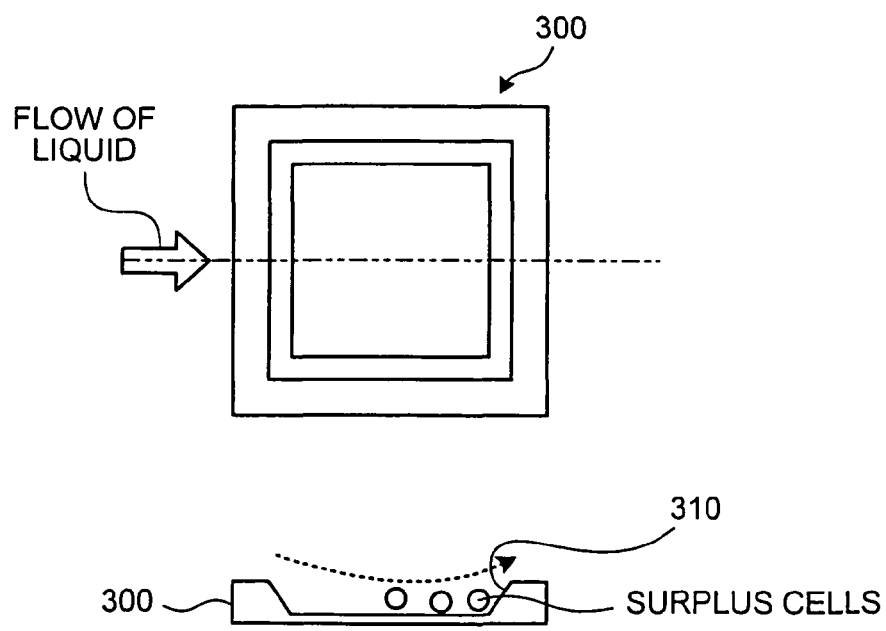
FIG. 15B is an explanatory diagram to explain another example of an orientation of the capturing plate.

As shown in FIG. 15B, although the capturing plate 300 is provided such that it is disposed nearly in parallel with the bottom wall 110 of the Petri dish 100, in this case, there is a certain degree of impairment of the empty cells collected by crossing the concave portion 310 in escaping due to the walls of the concave portion 310 during collection of the empty cells.

In focusing on this point, as shown in FIG. 15A, the fifth embodiment sets the direction of placement of the capturing plate 300 in the Petri dish 100 so as to be positioned where it is oriented at an angle of about 45 degrees to the flow of liquid (rotated on an angle to the liquid flow path). Namely, as shown in FIG. 15A, by setting the orientation of the capturing plate 300 to be about at an angle of 45 degrees, the angle of the walls of the concave portion 310 become smaller, thereby facilitating removal of the empty cells.

As has been explained above, since the direction in which the capturing plate 300 is placed in the Petri dish 100 in the fifth embodiment is set so as to be positioned at an angle of about 45 degrees, the flow during removal (collection) of the empty cells and collection of injected cells become linear, and in addition to enabling the collection efficiency of the empty cells to be improved, defective collection of the empty cells can be prevented.

Figure 16:
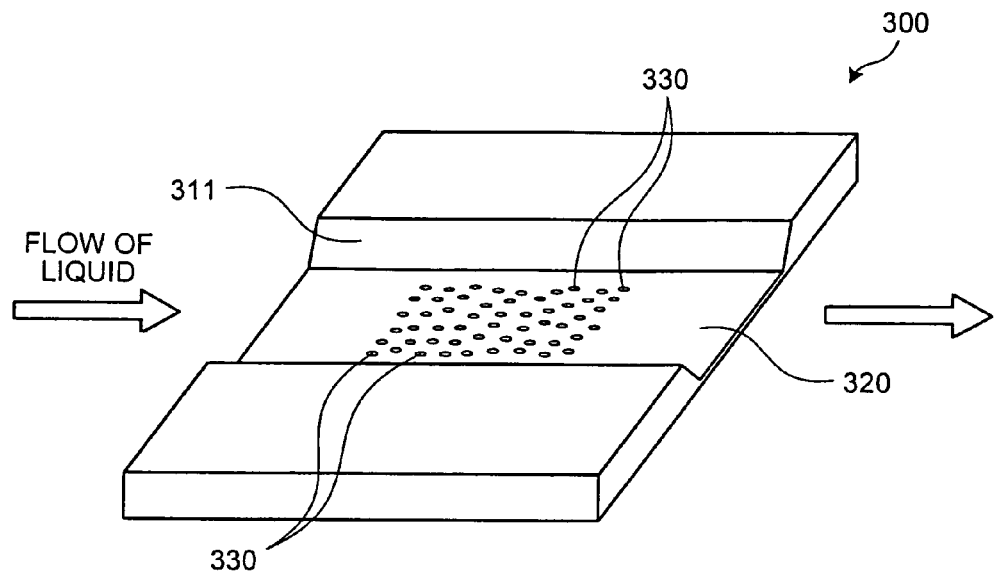
FIG. 16 is a perspective view of a capturing plate according to a sixth embodiment of the present invention.
Figure 17:
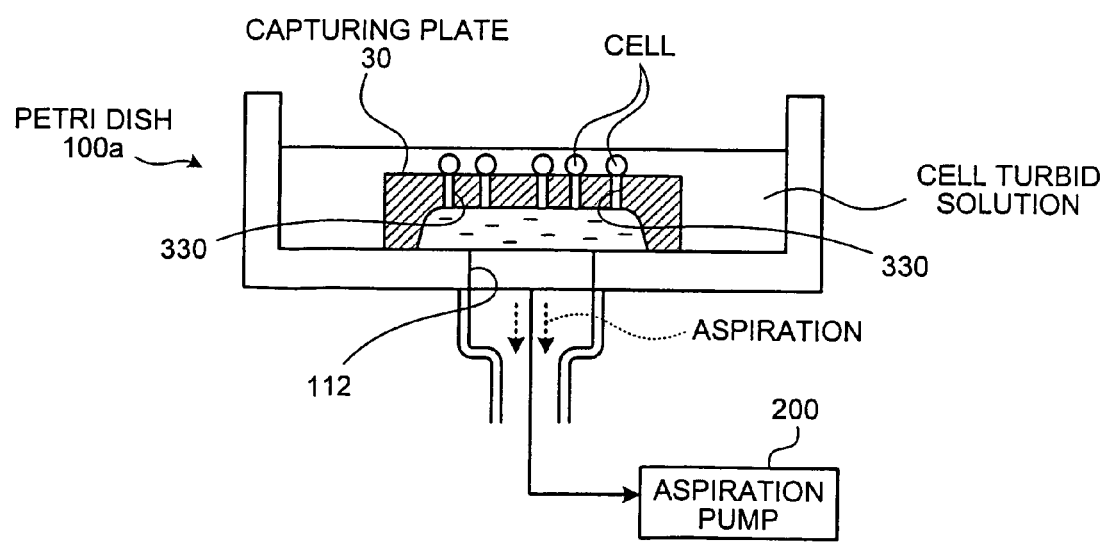
FIG. 17 is a longitudinal cross-section of relevant parts of a conventional Petri dish for capturing cells.

A sixth embodiment of the present invention is explained in detail with reference to FIG. 16. FIG. 16 is a schematic diagram of the constitution of the capturing plate 300 according to the sixth embodiment. Namely, as shown in FIG. 16, by making one of the thick portions of the concave portion formed on the capturing plate 300 to be thin, a part of the concave portion serves characteristically as a concave portion 311 that distributes the flow of liquid.

In the case of the capturing plate 300 according to the sixth embodiment, by forming a flow path in the capturing plate 300 by reducing the thickness of a thick portion of the capturing plate 300, in addition to resulting in a linear flow during removal (collection) of the empty cells and collection of injected cells, the collection efficiency of the empty cell and injected cells can be improved.

As has been explained above, since a distribution route is formed in the direction of flow in which liquid is distributed in one of the concave portions formed on the capturing plate 300 in the sixth embodiment, the flow of the removal (collection) of the empty cells and collection of injected cells becomes linear, thereby making it possible to improve the collection efficiency of the empty cells and injected cells.

According to an aspect of the present invention, it is possible to reliably prevent leakage. Moreover, it is possible to reliably and rapidly inject a predetermined amount of a substance into a large number of single cells. Furthermore, it is possible to observe cells easily and reliably with a transmitted light.

Moreover, because a fabrication step is carried out in which the back of the bottom wall of the cell capturing container is machined, and the formed flow groove is sealed with a transparent plate member, an aspiration flow path for capturing cells can be fabricated easily without causing increased costs.

Furthermore, because the aspiration flow path formed inside the cell capturing container employs a constitution that aspirates liquid with an aspirating unit disposed above, a microscope can be disposed below the transparent plate member. Accordingly, problems such as a contact between the needle used to aspirate cells and the microscope can be eliminated.

Moreover, injected cells and empty cells can be distinguished easily and reliably.

Furthermore, in addition to injected cells and empty cells inside the Petri dish being able to be distinguished easily, which has been unable to be carried out in conventional techniques, the necessary injected cells remain in the cell capturing plate, while unnecessary empty cells can be collected efficiently.

Moreover, mixing of empty cells and injected cells can be reliably prevented by improving the shielding action between the injected-cell collecting flow-path and the empty-cell collecting flow-path.

Furthermore, the separation distance between the transparent plate member and capturing plate can be reduced, the thickness at which the culture liquid (cell turbid solution) is filled can be reduced. Accordingly, decreases in optical resolution during microscopic observation can be prevented.

Although the invention has been described with respect to a specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. A cell capturing apparatus suitably used to capture a cell and inject a substance into captured cell while observing the cell under a microscope, comprising:
 a cell capturing container having a bottom wall and a side wall, the bottom wall including
  a first through hole;
  a second through hole; and
  a groove to connect ends of the first through hole and the second through hole that open on an outer surface of the bottom wall;
 a transparent plate member to cover a portion of the outer surface of the bottom wall including at least the first through hole, the second through hole, and the groove;
 a capturing plate disposed on an inner surface of the bottom wall and above the first through hole;
 an aspiration tube with one end to be connected to an upper portion of the second through hole and other end to be connected to an aspirating unit, to capture the cell in a micropore of the capturing plate by aspirating;
 an injected-cell collecting flow-path to connect a first discharge port for discharging liquid and a well to collect an injected cell in which the substance has been injected, and to guide the injected cell being captured in the micropore in a direction towards the well;
 an empty-cell collecting flow-path to connect a second discharge port for discharging liquid and a collection port for collecting an empty cell in which no substance has been injected, and to guide the empty cell near the capturing plate in a direction towards the collection port, which is different from the direction towards the well;

a pair of additional discharge ports that are provided on both sides of the second discharge port to discharge liquid to a direction parallel to the liquid discharged from the second discharge port before the second discharge port discharges liquid; and a collection pump provided at one end of the well, to switch aspiration pressure from positive pressure to negative pressure on the injected cell being guided by the injected-cell collecting flow-path, wherein the first discharge port and the second discharge port alternately discharge liquid.

2. The cell capturing apparatus according to claim 1, wherein the aspirating unit is to aspirate the liquid and the empty cell from the collection port.

3. The cell capturing apparatus according to claim 1, further comprising:

an obstruction member arranged in the empty-cell collecting flow-path between the second discharge port and the capturing surface of the capturing plate and to cause an obstruction in a flow of the liquid.

4. The cell capturing apparatus according to claim 1, wherein the empty-cell collecting flow-path between the second discharge port and the capturing surface of the capturing plate includes a plurality of empty-cell collecting sub-flow-paths.

5. The cell capturing apparatus according to claim 4, wherein the empty-cell collecting sub-flow-paths join together to form a single empty-cell collecting flow-path just before reaching the capturing surface of the capturing plate.

6. The cell capturing apparatus according to claim 1, further comprising:

a plurality of convex portions arranged in the empty-cell collecting flow-path between the second discharge port and the capturing surface of the capturing plate and causes an obstruction in a flow of the liquid.

7. The cell capturing apparatus according to claim 1, wherein a step is provided around the capturing surface of the capturing plate where the injected-cell collecting flow-path and the empty-cell collecting flow-path respectively intersect.

8. The cell capturing apparatus according to claim 1, wherein an inclination that prevents back flow of injected cells that have flowed into the well is provided at an intermediate position in the flow path that leads from the capturing surface of the capturing plate to the well on the downstream side of the injected-cell collecting flow-path.

9. The cell capturing apparatus according to claim 1, the capturing plate includes at least one capturing through hole for capturing the cell, wherein the cell capturing plate is disposed on the inner surface of the bottom wall in such a manner that the transparent plate member is located near the capturing through hole.

10. The cell capturing apparatus according to claim 1, wherein the capturing plate is disposed on the inner surface of the bottom wall in such a manner that the capturing plate makes an angle of about 45 degrees relative to a direction of the liquid flow along the empty-cell collecting flow-path.

* * * * *